United States Patent [19]

Emoto et al.

[11] Patent Number: 4,567,126
[45] Date of Patent: Jan. 28, 1986

[54] HYDRAZONE PHOTOCONDUCTIVE MATERIALS FOR ELECTROPHOTOGRAPHY

[75] Inventors: Kazuhiro Emoto; Kozo Haino, both of Nagaokakyo, Japan

[73] Assignee: Mitsubishi Paper Mills, Ltd., Tokyo, Japan

[21] Appl. No.: 675,743

[22] Filed: Nov. 28, 1984

[30] Foreign Application Priority Data

Dec. 1, 1983 [JP]  Japan .................. 58-227172
Dec. 1, 1983 [JP]  Japan .................. 58-227173

[51] Int. Cl.[4] .................. G03G 5/06; G03G 5/14
[52] U.S. Cl. .................. 430/59; 430/73; 430/74; 430/76; 430/77; 564/251
[58] Field of Search .................. 430/58, 59, 73, 74, 430/76, 77; 564/251

[56] References Cited

U.S. PATENT DOCUMENTS

| | | | |
|---|---|---|---|
| 4,150,987 | 4/1979 | Anderson et al. | 430/59 |
| 4,396,694 | 8/1983 | Nagata et al. | 430/74 X |
| 4,403,025 | 9/1983 | Horie et al. | 430/74 X |
| 4,413,045 | 11/1983 | Ishikawa et al. | 430/59 |
| 4,487,824 | 12/1984 | Katagiri et al. | 430/74 X |

*Primary Examiner*—Roland E. Martin
*Attorney, Agent, or Firm*—Cushman, Darby & Cushman

[57] ABSTRACT

Photoconductive materials for electrophotography which have high sensitivity and high durability are provided by incorporating at least one hydrazone compound represented by the following general formula (I) in photoconductive layer:

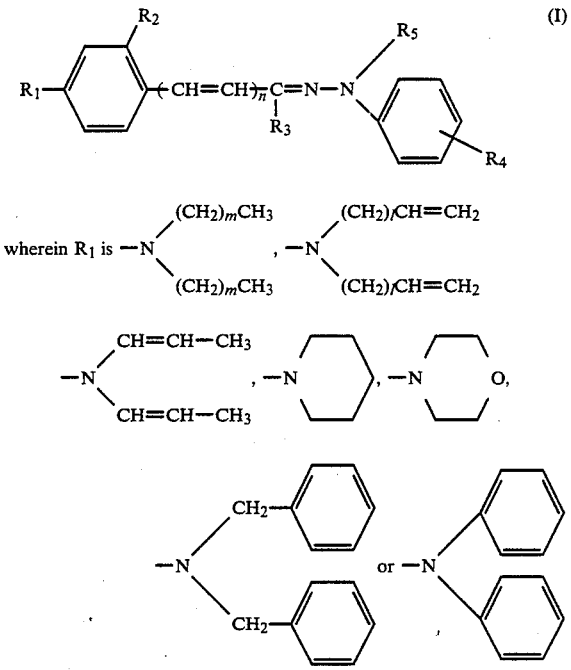

(wherein M is 0, 1, 2 or 3 and l is 1 or 2),
R$_2$ is a hydrogen atom, a lower alkyl group, a lower alkoxy group or a halogen atom,
R$_3$ is a hydrogen atom, a lower alkyl group or an aryl group,
R$_4$ is a hydrogen atom, a lower alkyl group, a lower alkoxy group or a halogen atom,
R$_5$ is an allyl group, propenyl group or

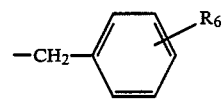

(wherein R$_6$ is a lower alkyl group, a lower alkoxy group or a halogen atom), and n is 0 or 1.

16 Claims, No Drawings

HYDRAZONE PHOTOCONDUCTIVE MATERIALS FOR ELECTROPHOTOGRAPHY

BACKGROUND OF THE INVENTION

This invention relates to a photoconductive material for use in electrophotography and, more particularly, to a photoconductive material comprising an electroconductive support and, formed thereon, a photoconductive layer incorporated with a hydrazone compound.

In conventional electrophotography, inorganic substances such as selenium, cadmium sulfide, amorphous silicon, and zinc oxide have been widely used in the photoconductive layer of photoconductive materials. In recent years, however, numerous researches are in progress to use organic photoconductive substances in photoconductive materials.

Fundamental properties required for the photoconductive materials to be used in electrophotography include (1) high charge acceptance when exposed to corona discharge in darkness, (2) low attenuation, in darkness, of the charge produced by corona discharge, (3) rapid dissipation of the charge when exposed to light, and (4) low residual charge after the exposure to light.

Selenium and cadmium sulfide widely used in conventional photoconductive materials are photoconductors which meet the above requirements with respect to fundamental properties. They have, however, disadvantages associated with their production such as, for example, high toxicity, difficulties encountered in film formation, lack of flexibility, and high cost. In view of the future exhaustion of natural resources, the production of inorganic substances will be limited. As a consequence as well as for the reason of environmental pollution originated from the toxic inorganic photoconductors, replacement of inorganic substances by organic photoconductors is desired. Under the circumstances, photoconductive materials prepared by using various organic substances have been proposed and some of them are in actual use. General advantages of organic photoconductors over inorganic substances are better transparency, lighter weight, easier film formation, ability to acquire both positive and negative charges, and easier fabrication.

Examples of typical organic photoconductors heretofore proposed include polyvinylcarbazole and derivatives thereof. These compounds, however, are not satisfactory in film-forming properties, flexibility, solubility, or adhesiveness. Although a certain degree of improvement was achieved by sensitizing polyvinylcarbazole with a pyrylium salt dye (Japanese Patent Publication No. 25,658/73) or with 2,4,7-trinitrofluorenone (U.S. Pat. No. 3,484,237), an organic photoconductor which meets the fundamental requirements mentioned above as well as required mechanical strengths and a sufficient durability has not yet been obtained.

SUMMARY OF THE INVENTION

The present inventors carried out an extensive study to obtain a photoconductive substance of high sensitivity and high durability and, as a result, found that a hydrazone compound represented by the following general formula (I) is an effective photoconductor and have accomplished the present invention.

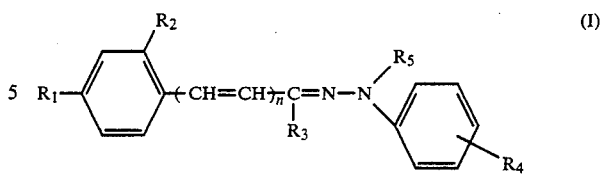

wherein $R_1$:

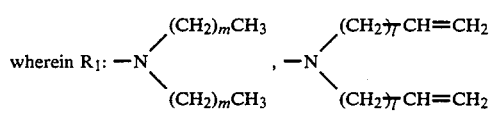

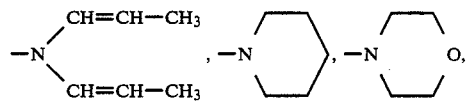

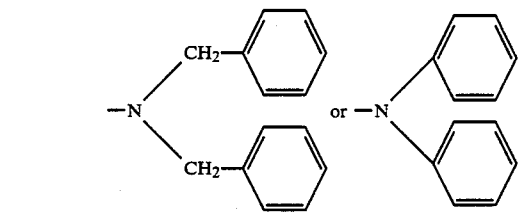

(wherein m is 0, 1, 2 or 3 and l is 1 or 2), $R_2$: hydrogen atom, a lower alkyl group, a lower alkoxy group or a halogen atom, $R_3$: hydrogen atom, a lower alkyl group or an aryl group, $R_4$: hydrogen atom, a lower alkyl group, a lower alkoxy group or a halogen atom, $R_5$: allyl group, propenyl group or

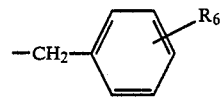

(wherein $R_6$: a lower alkyl group, a lower alkoxy group or a halogen atom),
and
n: 0 or 1.

DESCRIPTION OF THE INVENTION

The hydrazone compound of the general formula (I) according to this invention is generally synthesized by the following process:

A benzaldehyde derivative or a phenyl ketone derivative represented by the general formula (a) and a phenylhydrazine derivative represented by the general formula (b) are heated under reflux in a suitable solvent, e.g. an alcohol, in the presence of sodium (potassium) acetate or sodium (potassium) hydroxide as catalyst to synthesize a hydrazone compound represented by the general formula (c).

Reaction schedule:

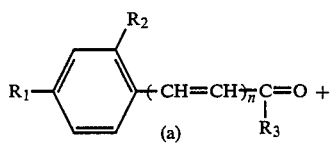

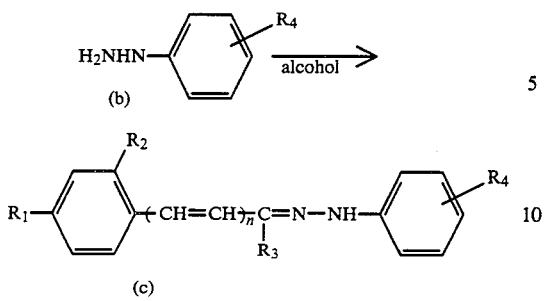

The hydrazone compound (c) thus formed and a compound represented by the general formula (d) are heated with stirring at 50° to 150° C. in the presence of an alkali as catalyst to obtain easily the hydrazone compound used in this invention.

$$R^5-X \quad (d)$$

In the above general formulas (a)–(d), $R_1$–$R_5$ and n are the same as defined above and X represents a halogen atom.

The above reaction proceeds in the absence of a solvent, but is generally carried out in an aqueous dimethyl sulfoxide or aqueous dimethylformamide.

Among the hydrazone compounds represented by the general formula (I), preferred as those represented by the following structural formulas wherein $R_1$–$R_6$ and l, m and n are the same as defined in general formula (I).

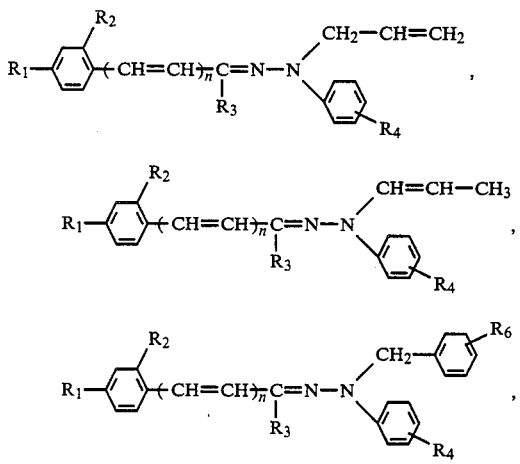

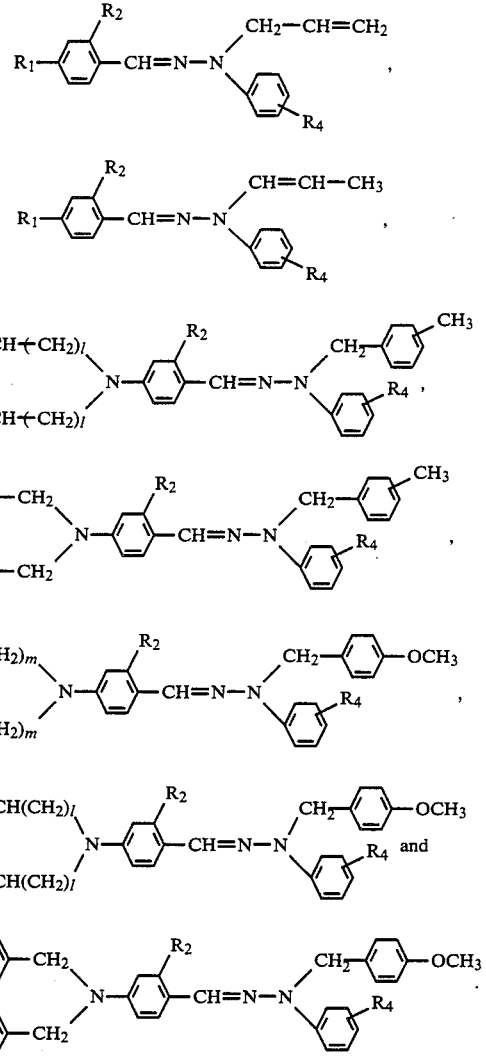

Among the hydrazone compounds represented by the general formula (I), the following compounds are preferred for the purpose of this invention in view of electrophotographic characteristics, solubility in organic solvents, stability to light and heat, economy, and convenience of synthesis.

| Compound No. | |
|---|---|
| 1 | 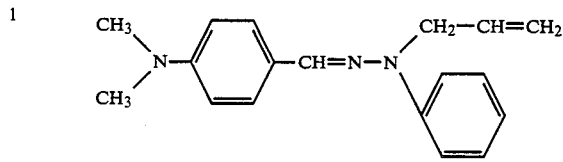 |

-continued
| Compound No. | |
|---|---|
| 2 | 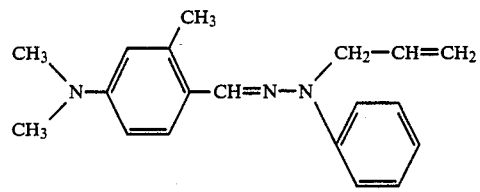 |
| 3 | 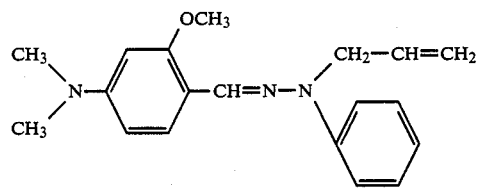 |
| 4 | 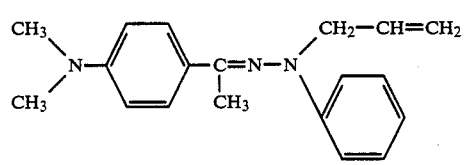 |
| 5 | 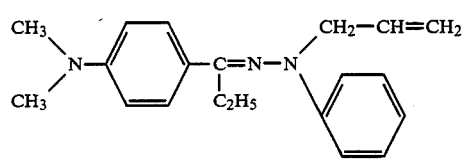 |
| 6 | 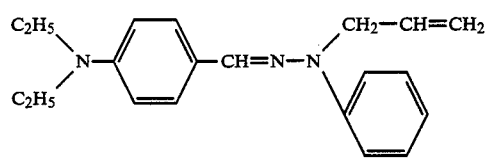 |
| 7 | 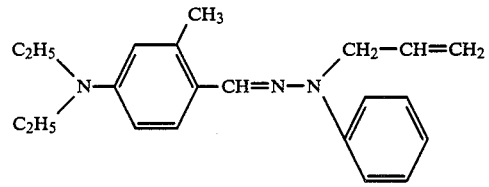 |
| 8 | 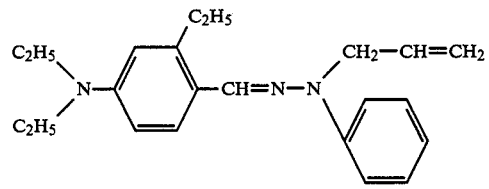 |
| 9 | 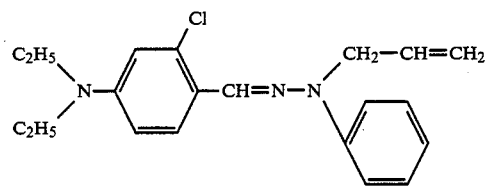 |

-continued
| Compound No. | |
|---|---|
| 10 | 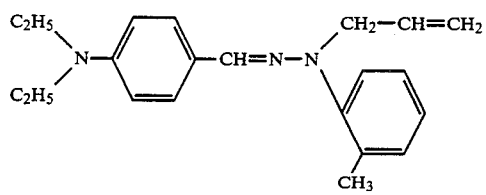 |
| 11 | 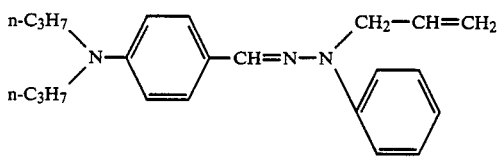 |
| 12 | 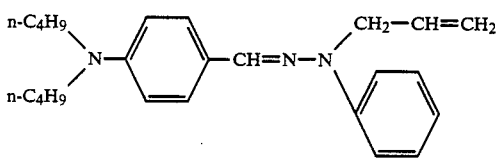 |
| 13 | 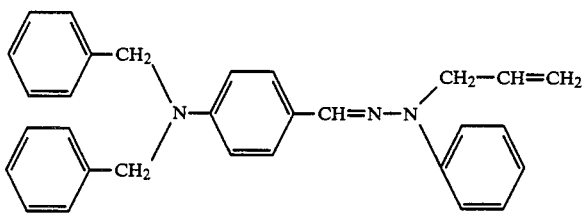 |
| 14 | 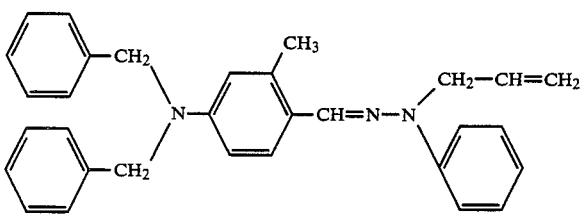 |
| 15 | 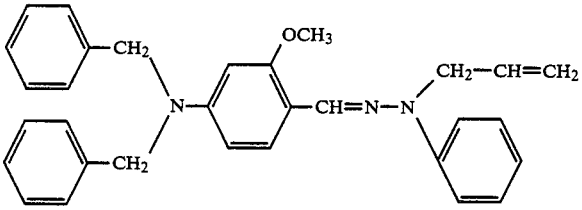 |
| 16 | 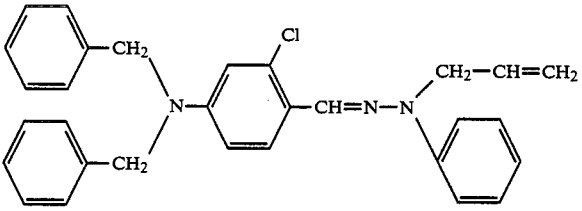 |

-continued
| Compound No. | |
|---|---|
| 17 | 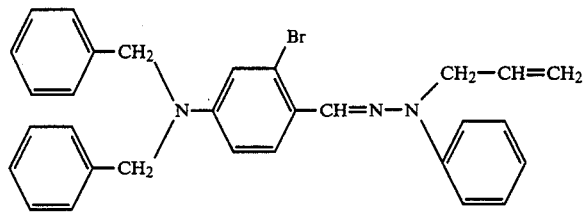 |
| 18 | 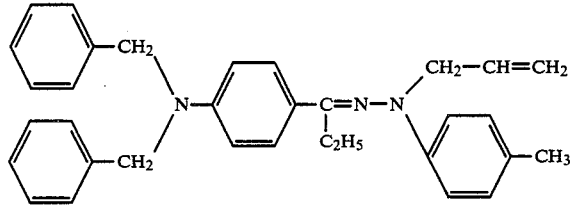 |
| 19 | 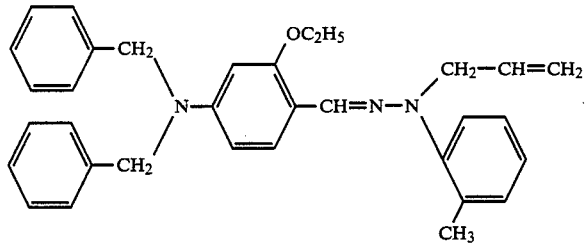 |
| 20 | 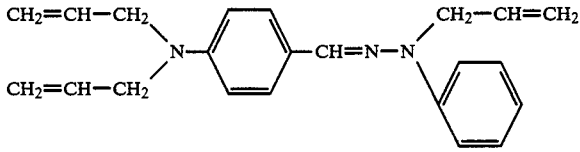 |
| 21 | 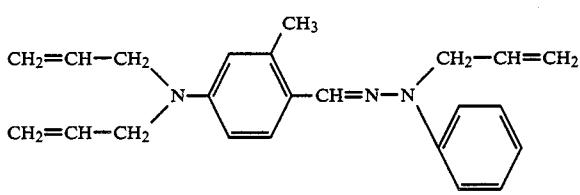 |
| 22 | 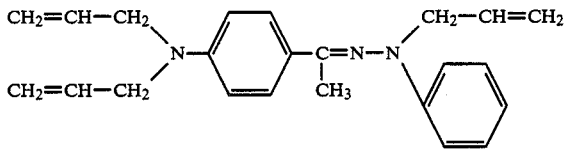 |
| 23 | 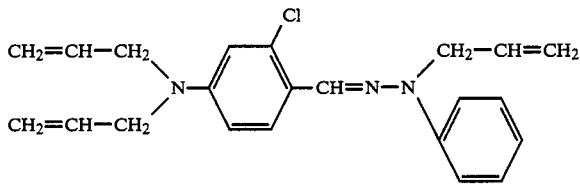 |

-continued
| Compound No. | |
|---|---|
| 24 | 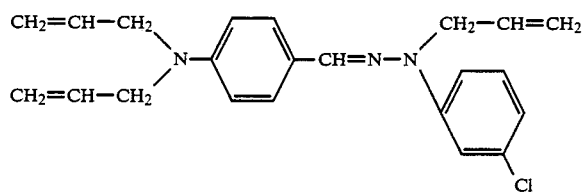 |
| 25 | 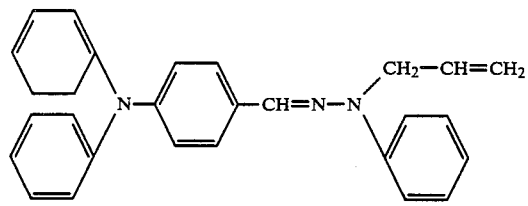 |
| 26 | 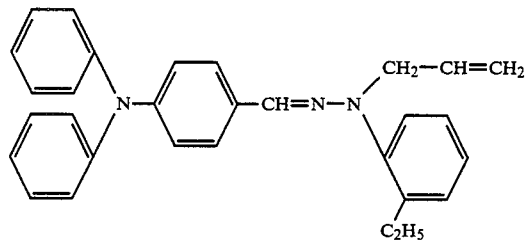 |
| 27 | 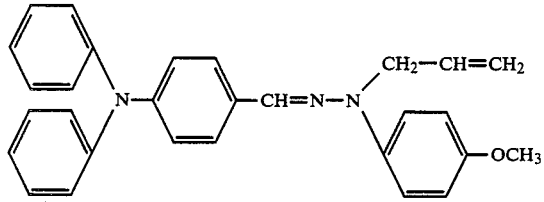 |
| 28 | 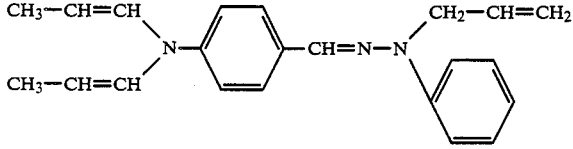 |
| 29 | 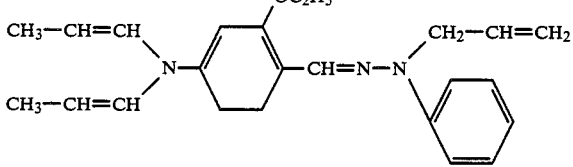 |
| 30 | 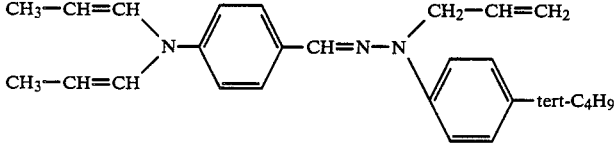 |
| 31 | 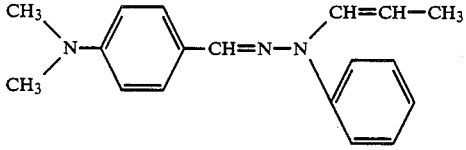 |

| Compound No. | |
|---|---|
| 32 | 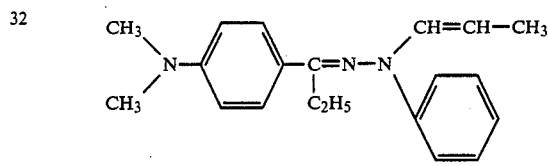 |
| 33 | 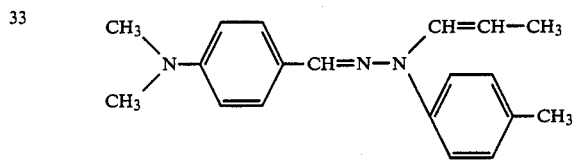 |
| 34 | 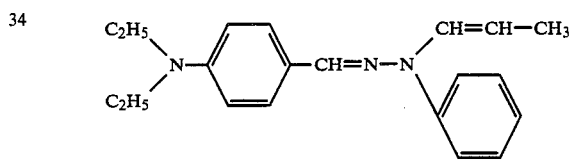 |
| 35 | 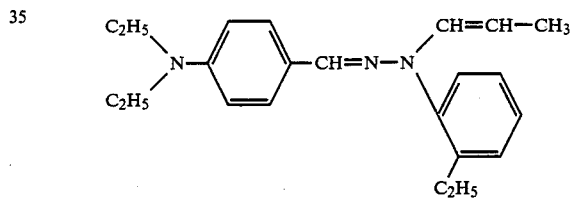 |
| 36 | 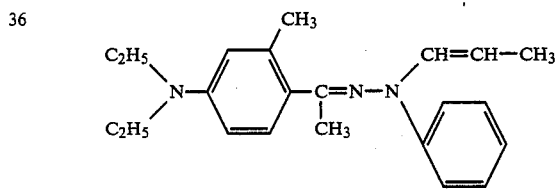 |
| 37 | 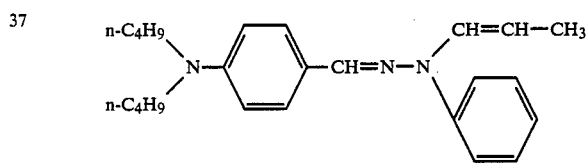 |
| 38 | 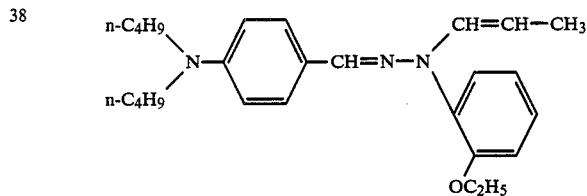 |
| 39 | 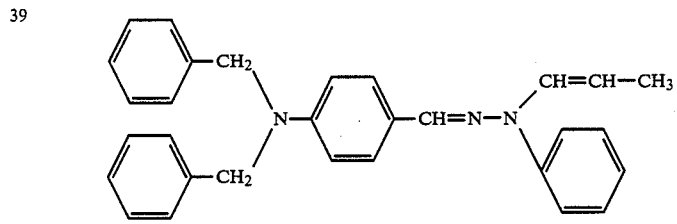 |

| Compound No. | |
|---|---|
| 40 | (C₆H₅-CH₂)₂N–[2-OCH₃-C₆H₃]–CH=N–N(CH=CH–CH₃)(C₆H₅) |
| 41 | (C₆H₅-CH₂)₂N–[2-OCH₃-C₆H₃]–CH=N–N(CH=CH–CH₃)(3-CH₃-C₆H₄) |
| 42 | (C₆H₅-CH₂)₂N–C₆H₄–C(CH₃)=N–N(CH=CH–CH₃)(C₆H₅) |
| 43 | (C₆H₅-CH₂)₂N–C₆H₄–CH=N–N(CH=CH–CH₃)(4-OC₂H₅-C₆H₄) |
| 44 | (CH₂=CH–CH₂)₂N–C₆H₄–CH=N–N(CH=CH–CH₃)(C₆H₅) |
| 45 | (CH₂=CH–CH₂)₂N–[2-OCH₃-C₆H₃]–CH=N–N(CH=CH–CH₃)(C₆H₅) |
| 46 | (CH₂=CH–CH₂)₂N–C₆H₄–C(CH₃)=N–N(CH=CH–CH₃)(C₆H₅) |

-continued
| Compound No. |
|---|
| 47 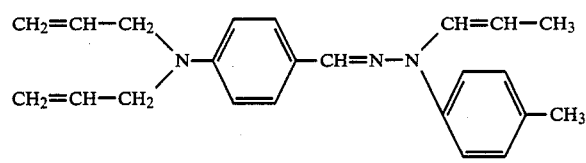 |
| 48 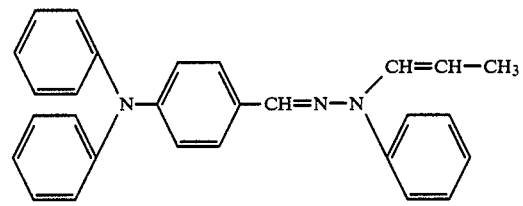 |
| 49 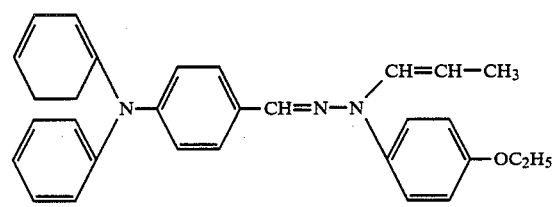 |
| 50 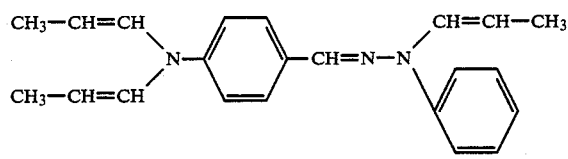 |
| 51 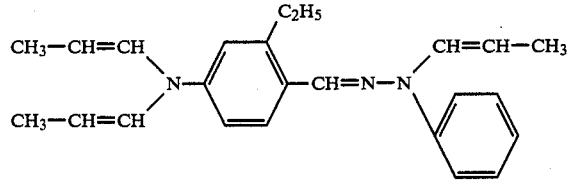 |
| 52 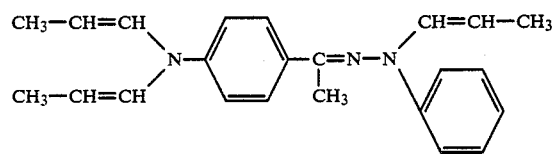 |
| 53 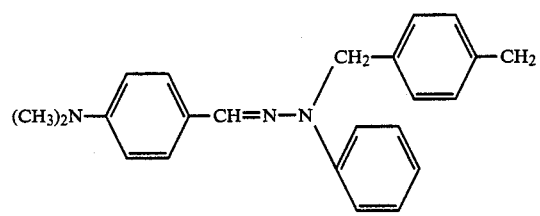 |
| 54 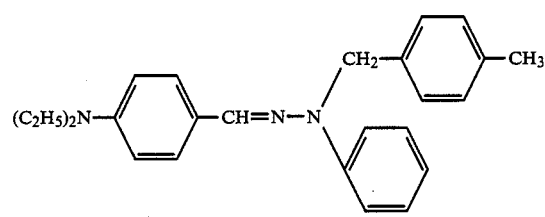 |

-continued
| Compound No. | |
|---|---|
| 55 | 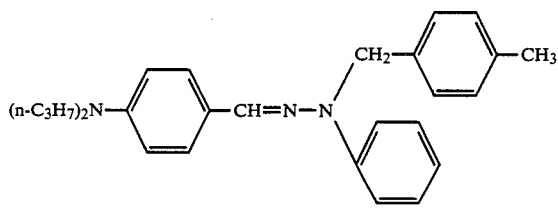 |
| 56 | 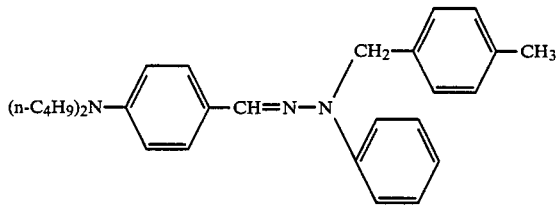 |
| 57 | 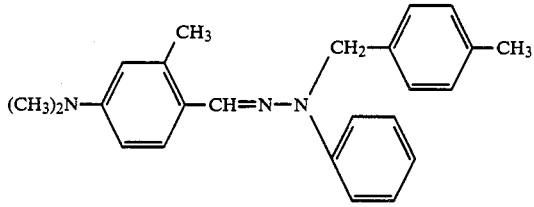 |
| 58 | 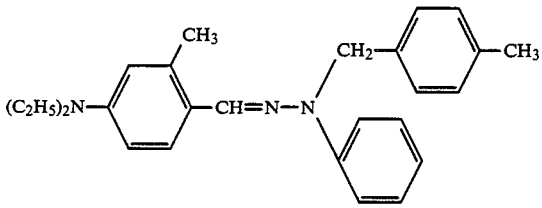 |
| 59 | 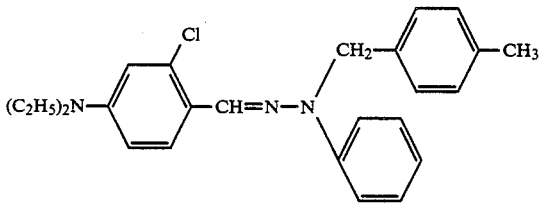 |
| 60 | 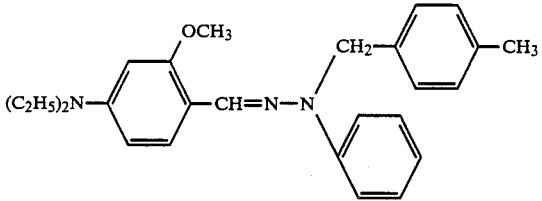 |
| 61 | 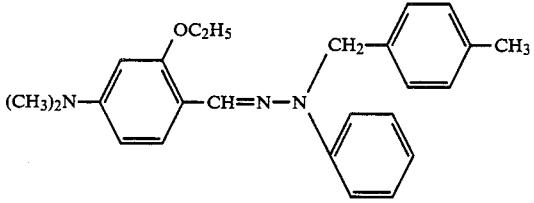 |

-continued
| Compound No. | |
|---|---|
| 62 | 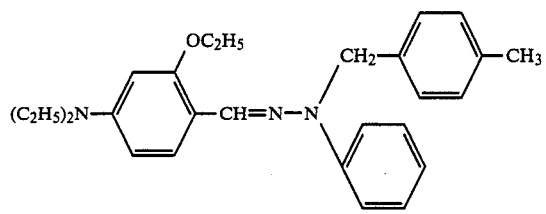 |
| 63 | 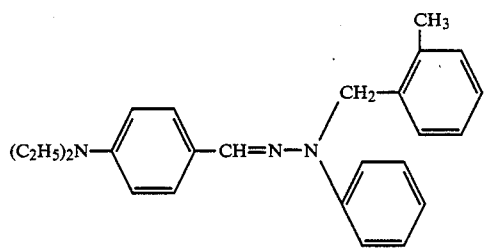 |
| 64 | 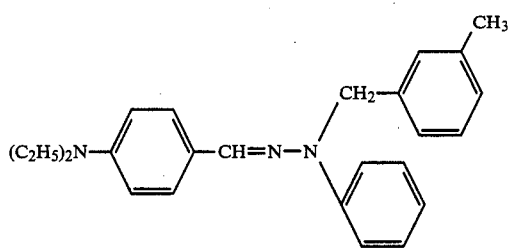 |
| 65 | 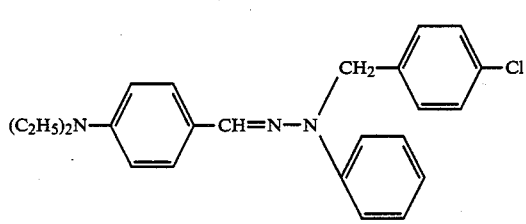 |
| 66 | 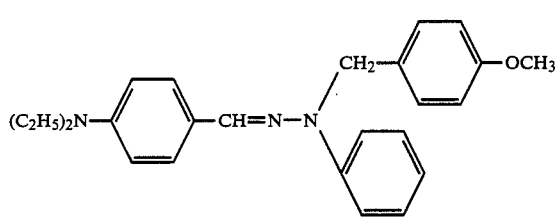 |
| 67 | 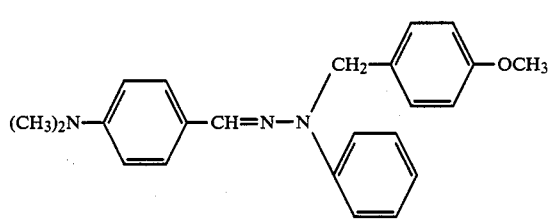 |

-continued
| Compound No. |
|---|
| 68 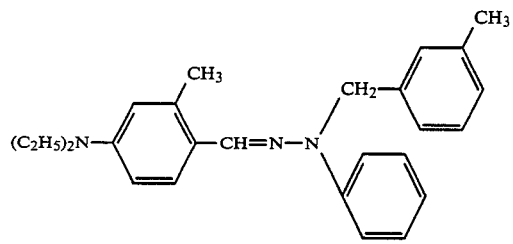 |
| 69 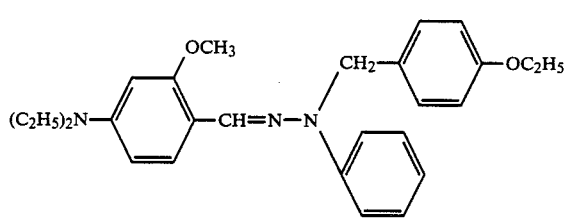 |
| 70 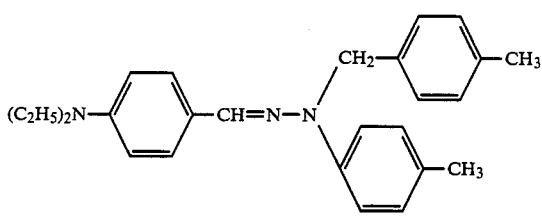 |
| 71 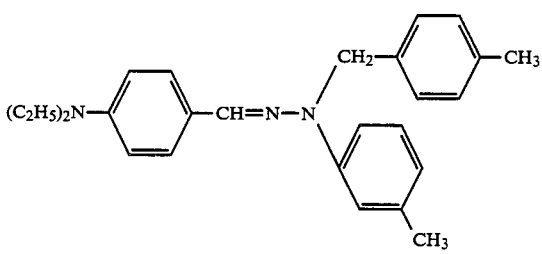 |
| 72 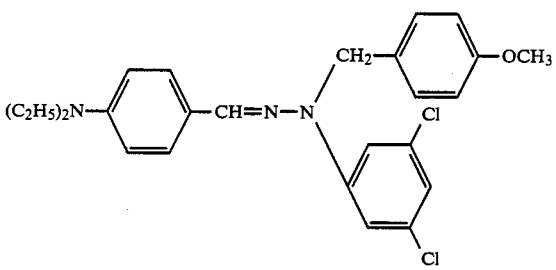 |
| 73 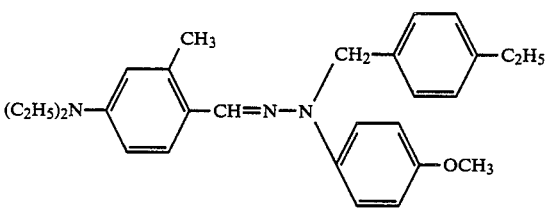 |

| Compound No. | |
|---|---|
| 74 | 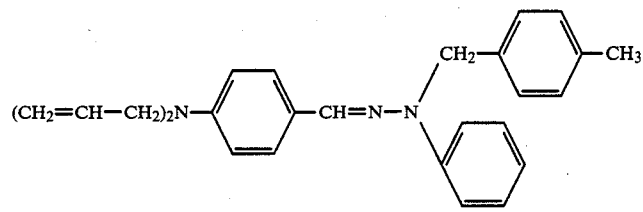 |
| 75 | 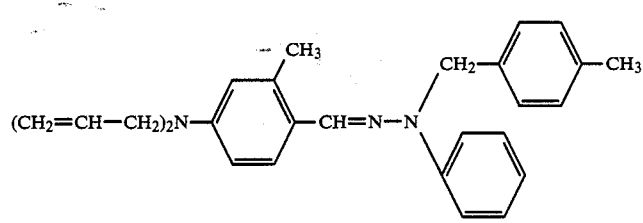 |
| 76 | 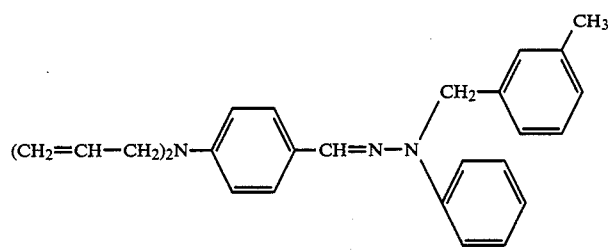 |
| 77 | 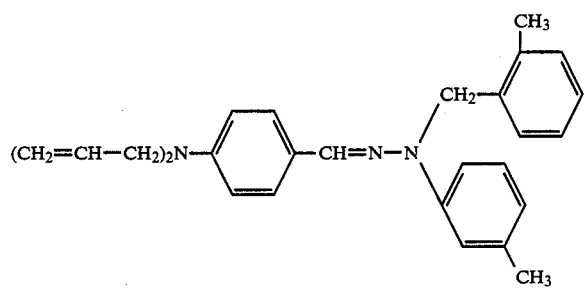 |
| 78 | 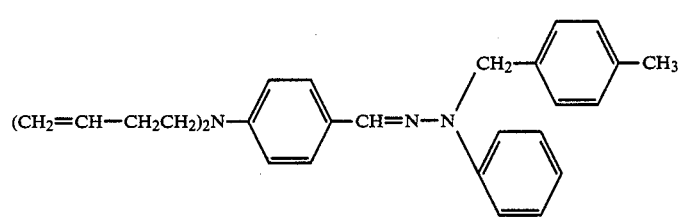 |
| 79 | 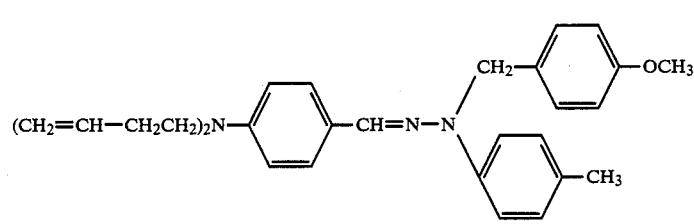 |

| Compound No. | |
|---|---|
| 80 | 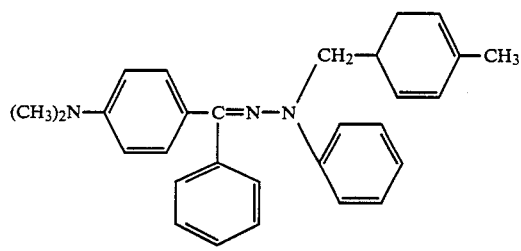 |
| 81 | 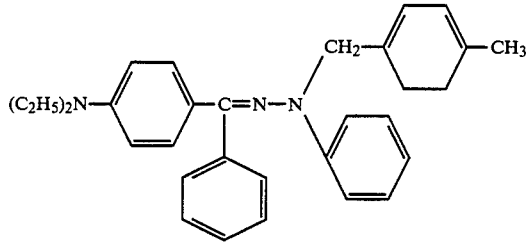 |
| 82 | 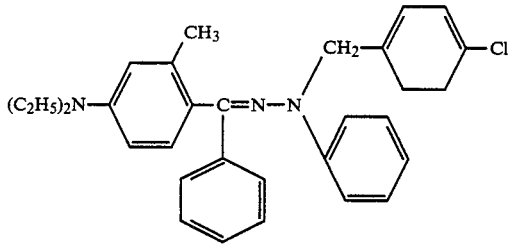 |
| 83 | 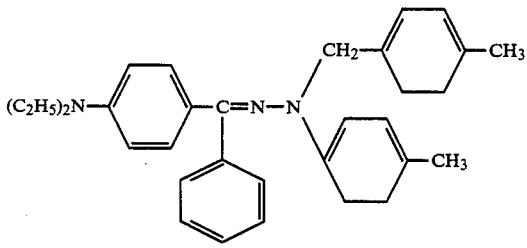 |
| 84 | 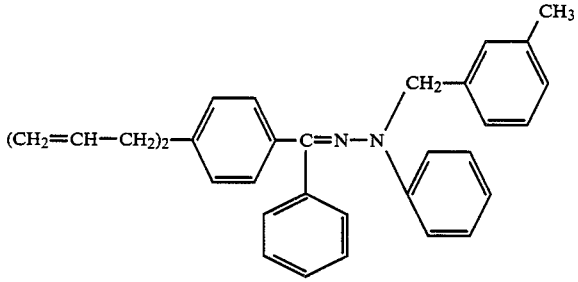 |
| 85 | 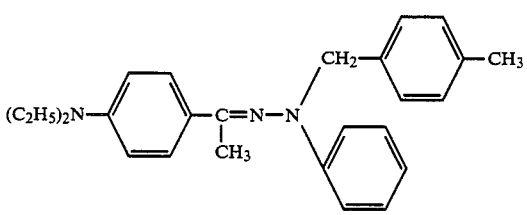 |

-continued

| Compound No. | |
|---|---|
| 86 | 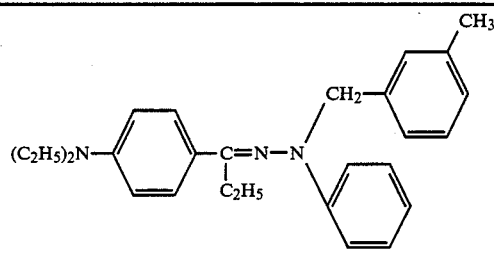 |
| 87 | 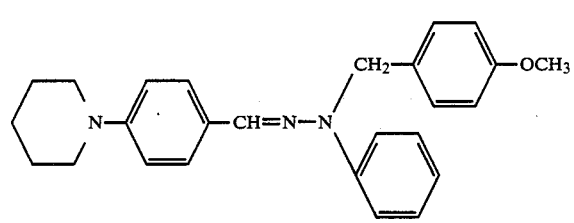 |
| 88 | 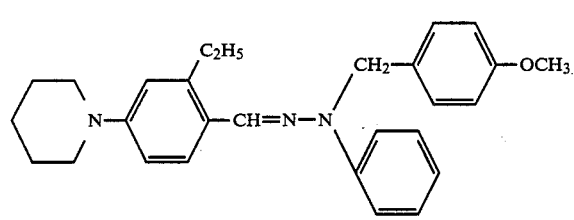 |
| 89 | 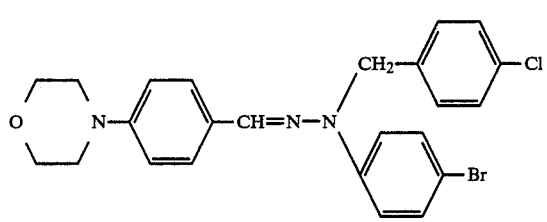 |
| 90 | 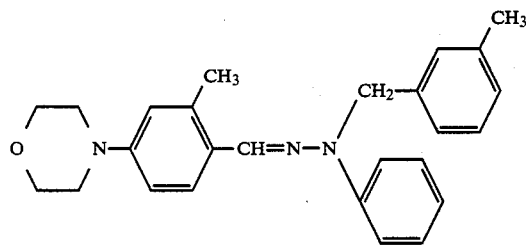 |

It is needless to say that the invention is not limited to those compounds listed above which are preferred for the abovementioned reasons. Synthetical Examples of some of the preferred compounds are described below.

SYNTHETICAL EXAMPLE 1 (Synthesis of compound No. 6)

Into a mixture of 20 cc of dimethyl sulfoxide and 5 cc of 5N sodium hydroxide solution, were added 4.8 g of allyl bromide and 5.4 g of diethylaminobenzaldehyde N-phenylhydrazone prepared by the equimolar reaction of N,N-dietylbenzaldehyde and phenylhydrazine in ethanol. The mixture was stirred for 2 hours at room temperature. After completion of the reaction, 50 cc of water was added to the reaction mixture to precipitate a solid substance. The solid substance was separated, washed with water, and recrystallized from 50 cc of methanol to yield 4.5 g of pale yellowish needle crystals melting at 103.5°–105.0° C. IR spectrum (KBr tablet method) showed disappearance of -NH-linking at 3300 $cm^{-1}$.

SYNTHETICAL EXAMPLE 2 (Synthesis of Compound No. 13)

In a manner similar to that in Synthetical Example 1, 7.6 g of N,N-dibenzylaminobenzaldehyde N-phenylhydrazone (melting point: 186.0°–188.0° C.) and 4.8 g of allyl bromide were added to a mixture of 5 cc of 5N sodium hydroxide solution and 30 cc of dimethyl sulfoxide. The mixture was stirred at room temperature for 2 hours. After completion of the reaction, 50 cc of water was added to the reaction mixture to precipitate a solid substance. The solid substance was separated, washed with water, and recrystallized from 240 cc of ethanol to yield 7.2 g of pale yellowish white needle crystals melting at 115°–177° C. IR spectrum (KBr tablet method) showed disappearance of -NH- linking at 3300 cm$^{-1}$.

SYNTHETICAL EXAMPLE 3 (Synthesis of compound No. 20)

To 1 mole of N,N-diallylaminobenzaldehyde in methanol, was added 1.2 moles of phenylhydrazine. The mixture was heated under reflux for about 2 hours to yield diallylaminobenzaldehyde N-phenylhydrazone (melting point: 63.5°–65.0° C.). Into a mixture of 5 cc of 5N sodium hydroxide solution and 20 cc of dimethyl sulfoxide, were added 5.0 g of said hydrazone and 4.8 g of allyl bromide. The mixture was stirred for 2 hours at room temperature. After completion of the reaction, 50 cc of water and ethyl acetate were added to the reaction mixture to extract the organic layer. The extract was freed from the ethyl acetate by distillation and the residue was recrystallized from 150 cc of alcohol to yield 3.8 g of pale yellowish white crystals melting at 38.5°–40.0° C.

The photoconductive material for electrophotography according to this invention, which has excellent performance characteristics, is prepared by the use of one or more of the above-mentioned compounds. Photoconductive materials of excellent performance are also obtained by use of a mixture of the above compounds with other hydrazone compounds (e.g. p-N,N-diethylaminobenzaldehyde N,N-diphenylhydrazone), oxadiazole compounds (e.g., 2,5-bis(p-diethylaminophenyl)-1,3,4-oxadiazole), or pyrazoline compounds (e.g. 1-p-diethylaminophenyl-3,5-diphenylpyrazoline).

The hydrazone compounds according to this invention can be used in any of the known types of photoconductive materials. For instance, an admixture of the hydrazone compound with a sensitizing dye and, if necessary, a chemical sensitizer or electron attracting compound is dissolved or dispersed in a binder and coated on a conductive support. In a type of laminated structure comprising a carrier generation layer of high charge carrier generation efficiency and a carrier transfer layer, a solution or dispersion of the hydrazone compound together with, if necessary, a chemical sensitizer or electron attracting compound is coated, as the carrier transfer layer, on a carrier generation layer which is provided on a conductive support and contains a sensitizing dye or pigment as major constituent.

In preparing a photoconductive material by use of the hydrazone compound according to this invention, the hydrazone compound is coated in the form of film with the aid of a polymeric film-forming binder on a support such as a sheet metal or a paper sheet or plastic film subjected to conductive treatment. It is preferable in this case to form a uniform photoconductive film by the addition of a sensitizer described later or a substance capable of plasticizing the polymeric film-forming binder.

The polymeric film-forming binder can be selected from a large number of substances, depending upon the use field of the photoconductive material. Desirable substances for use in the duplication field include such resins as polystyrene, styrene-butadiene copolymer, polyvinylacetal, diallylphthalate, silicone, polysulfone, polycarbonate, acrylic resins, methacrylic resins, vinyl acetate resin, vinyl chloride-crotonic acid copolymer, polyphenyleneoxide, polyesters, and alkyds. These resins, which can be homopolymer or copolymer, are used each alone or in combination of two or more. Of these resins, polystyrene, polyphenylene oxide, and polycarbonate are especially excellent in film characteristics and potential characteristics as a binder having a volume resistivity of $10^{12}$ ohm-cm or above. The weight ratio of such a binder to the organic photoconductor is in the range of from 0.2 to 20, preferably from 0.5 to 5. If the ratio is less than 0.5, the photoconductor will separate out of the photoconductive layer, while if it is larger than 5, a reduction in sensitivity will be resulted.

When the photoconductive material is intended for use in lithographic processes, a pro-alkaline binder is required. The term "pro-alkaline binder", as herein used, means a polymeric substance having an acidic group which has an affinity for an aqueous or alcoholic alkaline solution (or mixed solution). Examples of such acidic groups include acid anhydride group, carboxyl group, phenolic hydroxyl group, sulfonic acid group, sulfonamide group, and sulfonimide group. A binder having a high acid value of 100 or more is desirable, because it is readily soluble or swellable in the alkaline solvent. Examples of such binders include styrene-maleic anhydride copolymer, vinyl acetate-maleic anhydride copolymer, vinyl acetate-crotonic acid copolymer, (meth)-acrylic acid-(meth)acrylic ester copolymer, phenolic resin, and (meth)acrylic acid-styrene-(meth)acrylic ester copolymer. The ratio of such a resin to the photoconductor is roughly the same as that in the photoconductive material for use in reproduction processes.

Depending upon the type of polymeric film-forming binder, some binders give a hard and stiff photoconductive layer which is low in mechanical properties such as tensile, flexural, or compressive strength. In such a case, it becomes necessary to incorporate a plasticizing substance to improve the mechanical properties. As the plasticizing substances, mention may be made of phthalate esters such as, for example, dioctyl phthalate, dibutyl phthalate, and diisooctyl phthalate; phosphate esters such as, for example, tricresyl phosphate and trioctyl phosphate; sebacate esters, adipate esters, epoxydated soybean oil, nitrile rubber, and chlorinated hydrocarbons. The proportion of a plasticizing substance relative to the polymeric film-forming binder is preferably in the range of from 0.1% to 20% by weight. If the proportion is less than 0.1%, the improvement in mechanical properties will be insufficient, while if it exceeds 20%, the potential characteristics will be deteriorated.

The sensitizing dyes incorporated in the photoconductive layer include triphenylmethane dyes such as typically Methyl Violet, Crystal Violet, Ethyl Violet, Night Blue, and Victoria Blue; xanthene dyes such as typically Erythrosine, Rhodamine B, Rhodamine 3B, and Acridine Red B; acridine dyes such as typically Acridine Orange 2G, Acridine Orange R, and Flaveosine; thiazine dyes such as typically Methylene Blue, Methylene Green, and Methyl Violet; oxazine dyes such as typically Capri Blue; cyanine dyes, styryl dyes, pyrylium salts, and thiapyrylium salts.

As the photoconductive pigments capable of generating a charge carrier with a high efficiency upon absorption of light, there may be mentioned phthalocyanine pigments such as metal phthalocyanines and metal-free phthalocyanines; perylene pigments such as peryleneimide and perylenic anhydride; quinacridone pigments, azo pigments, and anthraquinone pigments. The dyes incorporated in the photoconductive layer can be used as a charge carrier generation substance. The dyes are used alone or in combination with a pigment. In the latter case, the efficiency of charge carrier generation is often enhanced. The inorganic photoconductive substances include selenium, selenium-tellurium alloy, cadmium sulfide, and zinc sulfide.

It is possible to add, in addition to the optical sensitizers listed above, a chemical sensitizer to further enhance the sensitivity. Examples of chemical sensitizers include p-chlorophenol, m-chlorophenol, p-nitrophenol, 4-chloro-m-cresol, p-chlorobenzoylacetanilide, N,N'-diethylbarbituric acid, N,N'-diethylthiobarbituric acid, 3-(β-oxyethyl)-2-phenyliminothiazolidone, malonic acid dianilide, 3,5,3',5'-tetrachloromalonic acid dianilide, α-naphthol, and p-nitrobenzoic acid.

It is also possible to incorporate into the photoconductive layer a certain type of electron-attracting compound which combines with the hydrazone compound forming a charge transfer complex, thus resulting in enhancement of the sensitization effect. Examples of such electron-attracting compounds include 1-chloroanthraquinone, 1-nitroanthraquinone, 2,3-dichloronaphthoquinone, 3,3'-dinitrobenzophenone, 4-nitrobenzalmalononitrile, phthalic anhydride, 3-(α-cyano-p-nitrobenzal)phthalide, 2,4,7-trinitrofluorenone, 1-methyl-4-nitrofluorenone, and 2,7-dinitro-3,6-dimethylfluorenone.

The photoconductive layer may contain other additives such as antioxidants and anticurling agents.

The photoconductive material of the present invention is prepared by dissolving or suspending the specified hydrazone compound together with other additives in a suitable solvent to form a coating composition which is then coated on an aforementioned conductive support and dried. Suitable solvents for the coating composition include aromatic hydrocarbons such as benzene, toluene, xylene and monochlorobenzene; chlorinated hydrocarbons such as chloroform, dichloroethane, and trichloroethylene; ethers such as dioxane and tetrahydrofuran; esters such as ethyl acetate and methyl "Cellosolve" acetate. These solvents are used each alone or in mixtures. If necessary, other solvents such as alcohols, acetonitrile, N,N-dimethylformamide, and methyl ethyl ketone may be added additionally.

The invention is illustrated below in detail with reference to Examples, but the invention is not limited thereto.

EXAMPLE 1

Using as the support an aluminum-clad polyester film (Alpet 85 of Mitsubishi Plastics Industries, Ltd.; 85μ in film thickness and 10μ in aluminum foil thickness), a n-butylamine solution containing 1% by weight of a bisazo pigment represented by the structure formula:

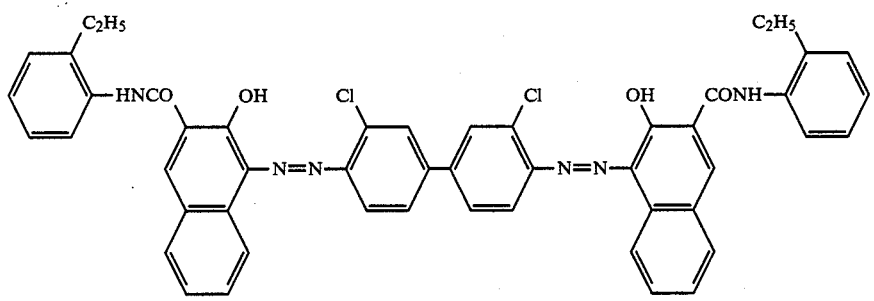

was coated on the support and dried to form a coating film of charge carrier generation substance of 0.2μ in thickness.

A dichloroethane solution containing 10% by weight of a mixture of each of hydrazone compounds No. 1 and No. 53 with a polycarbonate resin (Yupilon N-6 of Mitsubishi Gas Chemical Co.) (1:1.2 by weight) was coated, by means of an air knife, over the above film of carrier generation substance and dried to form a carrier transfer layer of 12μ in thickness.

The resulting lamination-type photoconductive materials for electrophotography were evaluated for the electrophotographic characteristics by means of an electrostatic recording sheet testing apparatus (SP-428 of Kawaguchi Denki Co.) under the conditions: applied potential −6 KV; Static −3. Upon exposure to white light, the charged specimen showed a high sensitivity of 2.5 lux.second in terms of exposure required for one-half light-decay of initial potential in case of compound No. 1 and 3.5 lux.second in case of Compound No. 53. After the same test by means of the same apparatus had been repeated $10^3$ or more times, there was noticed no deterioration in the electrophotographic characteristics including the said sensitivity.

EXAMPLES 2 to 20

Lamination-type photoconductive materials were prepared in the same manner as in Example 1, except that hydrazone compounds shown in Table 1 were used in place of the hydrazone compounds No. 1 and No. 53. Each photoconductive material thus prepared was tested for the one-half light-decay exposure and the initial potential, in volt, under the same conditions as in Example 1. The results obtained were as shown in Table 1. In Table 1 are shown also the initial potential, in volt, and the sensitivity in terms of half light-decay exposure after 1,000 charging-discharging cycles (discharging was performed by exposure to white light of 400 lux for one second). It is seen from Table 1 that the present photoconductive material comprising the hydrazone compound is excellent in sensitivity and recycle characteristics.

TABLE 1

| | | 1st cycle | | 1,000 th cycle | |
|---|---|---|---|---|---|
| Example No. | Hydrazone compound No. | Initial potential | Half light-decay exposure (lux · sec) | Initial potential | One-half light-decay exposure (lux · sec) |
| 2 | 2 | 1070 | 3.5 | 990 | 3.3 |
| 3 | 4 | 1120 | 4.7 | 1090 | 4.2 |
| 4 | 6 | 990 | 2.6 | 970 | 2.4 |
| 5 | 8 | 1040 | 3.6 | 1010 | 3.3 |
| 6 | 10 | 1010 | 3.0 | 970 | 2.7 |
| 7 | 13 | 1090 | 2.6 | 1030 | 2.5 |
| 8 | 21 | 870 | 2.7 | 820 | 2.1 |

TABLE 1-continued

| Example No. | Hydrazone compound No. | 1st cycle Initial potential | 1st cycle Half light-decay exposure (lux · sec) | 1,000th cycle Initial potential | 1,000th cycle One-half light-decay exposure (lux · sec) |
|---|---|---|---|---|---|
| 9  | 37 | 920  | 3.2 | 880  | 3.0 |
| 10 | 39 | 1000 | 4.0 | 980  | 3.7 |
| 11 | 54 | 980  | 2.5 | 960  | 2.5 |
| 12 | 56 | 940  | 2.5 | 910  | 2.5 |
| 13 | 58 | 1020 | 2.5 | 1000 | 2.5 |
| 14 | 60 | 990  | 3.0 | 970  | 3.0 |
| 15 | 66 | 940  | 2.5 | 900  | 2.5 |
| 16 | 73 | 910  | 2.5 | 890  | 2.0 |
| 17 | 76 | 1020 | 2.5 | 990  | 2.5 |
| 18 | 79 | 900  | 3.0 | 830  | 2.0 |
| 19 | 80 | 1050 | 3.0 | 1030 | 3.0 |
| 20 | 85 | 930  | 3.5 | 890  | 3.0 |

EXAMPLE 21

A lamination-type photoconductive material was prepared in the same manner as in Example 1, except that a trisazo pigment of the following structural formula was used in place of the bisazo pigment:

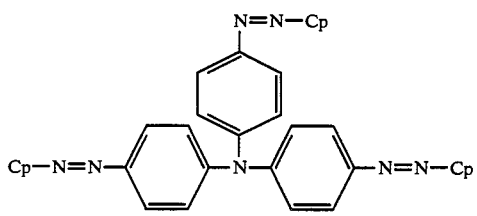

wherein Cp =

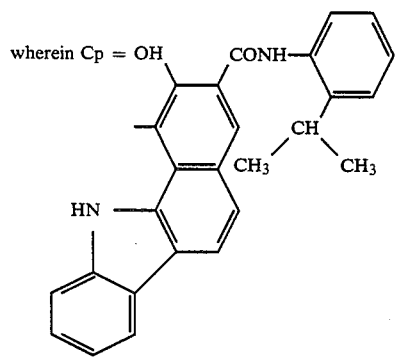

The resulting photoconductive materials were tested for the spectral sensitivity at 633 nm (He-Ne laser) and 680 nm (light-emitting diode) by means of a monochrometer. The energy required for the one-half decay of initial potential was 3.5 erg/cm² (633 nm) and 3.2 erg/cm² (680 nm), in case of compound No. 1 and 3.9 erg/cm² (633 nm) and 3.6 erg/cm² (680 nm) in case of compound No. 53, respectively, indicative of high sensitivities.

EXAMPLES 22 TO 40

Into 30 ml of a solution containing 0.1 g of a polyarylate resin (V-100 of Unitika Ltd.) dissolved in dichloromethane, was added 0.2 g of the same trisazo pigment as used in Example 21. The mixture was dispersed in a paint conditioner (Red Label Co.) for about 20 minutes. The resulting dispersion was coated, by means of a doctor blade, on a sheet of Alpet 85 to a dry thickness of 0.4μ to form a charge generation layer. A photoconductive material was prepared by laminating a charge transfer layer containing one of the hydrazone compounds used in Examples 2 to 20 onto the said charge generation layer. Each of the resulting photoconductive materials was tested for the spectral sensitivities at 633 and 680 nm in the same manner as in Example 21. The energy required for the one-half decay of initial potential of each material was as shown in Table 2.

TABLE 2

| Example No. | Hydrazone compound No. | Energy for one-half decay of potential (erg/cm²) 630 nm | Energy for one-half decay of potential (erg/cm²) 680 nm |
|---|---|---|---|
| 22 | 2  | 3.1 | 3.0 |
| 23 | 4  | 4.0 | 3.6 |
| 24 | 6  | 2.8 | 2.7 |
| 25 | 8  | 3.5 | 3.2 |
| 26 | 10 | 3.2 | 3.0 |
| 27 | 13 | 2.7 | 2.7 |
| 28 | 21 | 2.8 | 2.6 |
| 29 | 37 | 3.0 | 2.9 |
| 30 | 39 | 3.8 | 3.7 |
| 31 | 54 | 3.1 | 3.0 |
| 32 | 56 | 3.0 | 2.7 |
| 33 | 58 | 2.8 | 2.7 |
| 34 | 60 | 3.5 | 3.2 |
| 35 | 66 | 2.9 | 2.6 |
| 36 | 73 | 2.7 | 2.7 |
| 37 | 76 | 2.8 | 2.6 |
| 38 | 79 | 3.6 | 3.4 |
| 39 | 80 | 3.8 | 3.7 |
| 40 | 85 | 4.8 | 4.5 |

It is understood from the above results that each photoconductive material showed spectral sensitivities below 5.0 erg/cm² at 630 and 680 nm, indicative of excellent performance. None of the materials required an energy exceeding 20 erg/cm² to bring the residual potential to zero level when tested at either 630 or 680 nm.

EXAMPLE 41

A mixture of 0.3 g of the same trisazo pigment used in Example 21 and 0.05 g of a polymethine dye of the following structure was dispersed in dichloroethane (the polymethine dye dissolved completely):

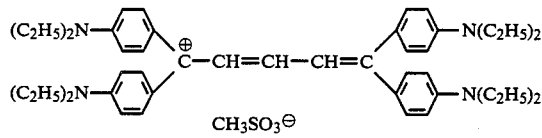

A 10% polyarylate resin solution was added to the dispersion so that the total solids content may become 3%, and the mixture was again dispersed in a paint conditioner for about one hour. The resulting suspension was applied onto a sheet of Alpet 85 to form a coating layer of 0.3μ in dry thickness. The resulting carrier generation layer was overcoated with the same hydrazone compound solution as used in Example 21 so that a carrier transfer layer of about 13μ in dry thickness may be formed.

The electrophotographic conductive material thus formed was tested for spectral sensitivities at 780, 800 and 830 nm in the same manner as in Example 21. The sensitivities were found to be 3.7, 3.4, and 3.2 erg/cm² in case of compound No. 1 and 4.0, 3.6 and 3.4 erg/cm² in case of compound No. 53, respectively, which prove the material to be highly sensitive even in the near-infrared regions.

EXAMPLE 42

A mixture was prepared from 1.5 parts by weight of a styrene-maleic anhydride copolymer (50 mole-% in styrene unit content), 1 part by weight of each of hydrazone compound No. 12, and No. 64 and $5\times10^{-3}$ part by weight of 4-(4-diethylaminophenyl)-2,6-diphenylthiapyrylium fluoroborate (a thiapyrylium salt dye). The mixture was dissolved in dioxane to form a 10% by weight solution. The resulting solution was coated, by means of S-doctor, on an anodized aluminum sheet which had been grained, and then dried to prepare a single-layered photoconductive material of about 5μ in thickness of coating layer. The photoconductive material thus obtained was evaluated for electrophotographic characteristics by means of the aforementioned electrostatic recording paper testing apparatus, under the conditions: applied potential $-6$ KV; static $-3$. It was found that the initial voltage was $-480$ V and the one-half light-decay exposure was 5.3 lux.second in case of compound No. 12 and the initial voltage was $-480$ V and the one-half light-decay exposure was 6.0 lux.second in case of compound No. 64.

The above photoconductive material was developed with a toner to visualize the latent electrostatic image, and then treated with an alkaline processing solution such as, for example, an aqueous solution containing 3% of triethanolamine, 10% of ammonium carbonate, and 20% of polyethylene glycol having an average molecular weight of 190-210. The coating in the undeveloped areas, where no toner was present, readily dissolved away. Upon washing with an aqueous solution containing sodium silicate, there was obtained a lithographic printing plate. This printing plate was found to endure printing of about 100,000 copies on an off-set press.

In the above experiment, an optimum exposure (a halogen lamp as light source) was 50 lux.0.3 second in case of compound No. 12 and 50 lux.0.5 second in case of compound No. 64. The printing plate was made by the direct process without finish work.

EXAMPLE 43

In a manner similar to that in Example 42, single-layered photoconductive materials, about 4μ in thickness of coating layer, were prepared by adding $10^{-1}$ part by weight of ε-type copper phthalocyanine in place of the thiapyrylium salt dye to 1 part by weight of the hydrazone compounds, and treating the mixture in a ball mill to disperse thoroughly the phthalocyanine. The electrophotographic characteristics of the resulting photoconductive materials were found to be as follows: initial potential $+380$ V; one-half light-decay exposure 6.2 lux.second. Printing plates were prepared similarly to Example 42 by successive exposure, development, alkali treatment, and water washing. The resulting printing plate was found to endure printing of about 100,000 copies. The exposure was performed using as light source a monochromatic light of 633 nm. The optimum irradiation was about 80 erg/cm² in case of compound No. 12 and about 65 erg/cm² in case of compound No. 64.

What is claimed is:

1. A photoconductive material for electrophotography comprising an electroconductive support and, formed thereon, a photoconductive layer incorporated with at least one hydrazone compound represented by the general formula (I):

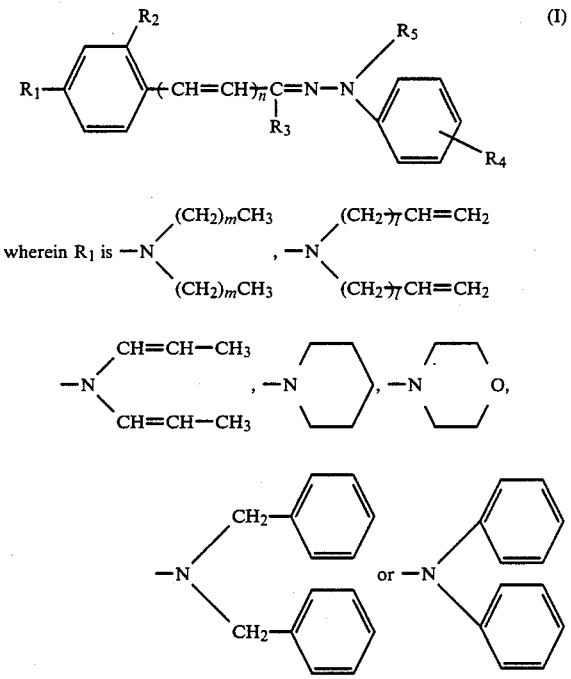

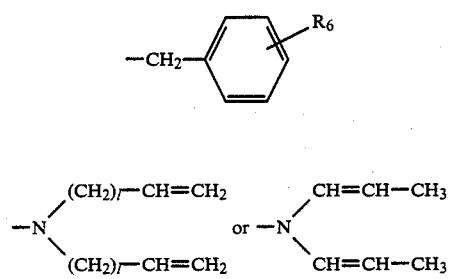

provided that $R_1$ must be

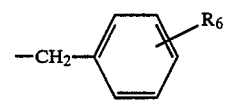

(wherein $R_6$ is a lower alkyl group, a lower alkoxy group or a halogen atom), and n is 0 or 1.

2. A photoconductive material for electrophotography according to claim 1, wherein the photoconductive layer contains a carrier transfer substance and a carrier generating substance and said carrier transfer substance is at least one hydrazone compound represented by the general formula (I).

3. A photoconductive material for electrophotography according to claim 1, wherein the hydrazone compound represented by the general formula (I) is a compound represented by the structural formula $$R_1\text{---}\underset{R_2}{\bigcirc}\text{---}(CH=CH)_n\underset{R_3}{C}=N\text{---}N\underset{R_4}{\diagdown}\overset{CH_2\text{---}CH=CH_2}{\bigcirc}$$

wherein $R_1$, $R_2$, $R_3$ and $R_4$ and n are as defined in claim 1.

4. A photoconductive material for electrophotography according to claim 1, wherein the hydrazone compound represented by the general formula (I) is a compound represented by the structural formula $$R_1\text{---}\underset{R_2}{\bigcirc}\text{---}(CH=CH)_n\underset{R_3}{C}=N\text{---}N\underset{R_4}{\diagdown}\overset{CH=CH\text{---}CH_3}{\bigcirc}$$

wherein $R_1$, $R_2$, $R_3$ and $R_4$ and n are as defined in claim 1.

5. A photoconductive material for electrophotography according to claim 1, wherein the hydrazone compound represented by the general formula (I) is a compound represented by the structural formula $$R_1\text{---}\underset{R_2}{\bigcirc}\text{---}(CH=CH)_n\underset{R_3}{C}=N\text{---}N\underset{R_4}{\diagdown}\overset{CH_2\text{---}\bigcirc\text{---}R_6}{\bigcirc}$$

where $R_2$, $R_3$, $R_4$ and $R_6$ and n are defined in claim 1, and $R_1$ is either $$-N\begin{matrix}(CH_2)_r\text{---}CH=CH_2\\(CH_2)_r\text{---}CH=CH_2\end{matrix} \quad \text{or} \quad -N\begin{matrix}CH=CH\text{---}CH_3\\CH=CH\text{---}CH_3\end{matrix}$$

6. A photoconductive material for electrophotography according to claim 1, wherein the hydrazone compound represented by the general formula (I) is a compound represented by the structural formula $$R_1\text{---}\underset{R_2}{\bigcirc}\text{---}CH=N\text{---}N\underset{R_4}{\diagdown}\overset{CH_2\text{---}CH=CH_2}{\bigcirc}$$

wherein $R_1$, $R_2$ and $R_4$ are as defined in claim 1.

7. A photoconductive material for electrophotography according to claim 1, wherein the hydrazone compound represented by the general formula (I) is a compound represented by the structural formula $$R_1\text{---}\underset{R_2}{\bigcirc}\text{---}CH=N\text{---}N\underset{R_4}{\diagdown}\overset{CH=CH\text{---}CH_3}{\bigcirc}$$

wherein $R_1$, $R_2$ and $R_4$ are as defined in claim 1.

8. A photoconductive material for electrophotography according to claim 1, wherein the hydrazone compound represented by the general formula (I) is a compound represented by the structural formula $$\begin{matrix}CH_2=CH\text{+}CH_2)_l\\CH_2=CH\text{+}CH_2)_l\end{matrix}N\text{---}\underset{R_2}{\bigcirc}\text{---}CH=CH\text{---}N\underset{\bigcirc\text{---}R_4}{\diagdown}\overset{CH_2\text{---}\bigcirc\text{---}CH_3}{\bigcirc}$$

wherein $R_2$ and $R_4$ and l are as defined in claim 1.

9. A photoconductive material for electrophotography according to claim 1, wherein the hydrazone compound represented by the general formula (I) is a compound represented by the structural formula $$\begin{matrix}CH_2=CH(CH_2)_l\\CH_2=CH(CH_2)_l\end{matrix}N\text{---}\underset{R_2}{\bigcirc}\text{---}CH=N\text{---}N\underset{\bigcirc\text{---}R_4}{\diagdown}\overset{CH_2\text{---}\bigcirc\text{---}OCH_3}{\bigcirc}$$

wherein $R_2$ and $R_4$ and l are as defined in claim 1.

10. A photoconductive material for electrophotography according to claim 2, wherein the carrier generation substance is a trisazo pigment.

11. A photoconductive material for electrophotography according to claim 2, wherein the carrier generation substance is a bisazo pigment.

12. A photoconductive material for electrophotography according to claim 2, wherein the carrier generation substance is a phthalocyanine pigment.

13. A photoconductive material for electrophotography according to claim 2, wherein the photoconductive layer is of laminate structure comprising a carrier generating layer and a carrier transfer layer provided thereon.

14. An electrophotographic process which comprises imagewise exposing the photoconductive material of calim 1 which has been charged and then developing it.

15. A photoconductive material for electrophotography comprising an electroconductive support and, formed thereon, a photoconductive layer incorporated with at least one hydrazone compound represented by the general formula (I):

$$R_1\text{---}\underset{R_2}{\bigcirc}\text{---}(CH=CH)_n\underset{R_3}{C}=N\text{---}N\underset{R_4}{\diagdown}\overset{R_5}{\bigcirc} \tag{I}$$

-continued wherein $R_1$[:] is 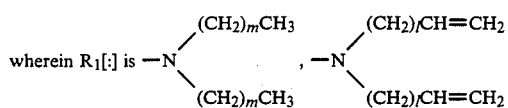,

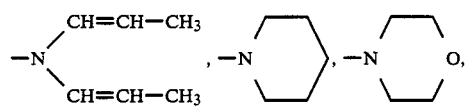,

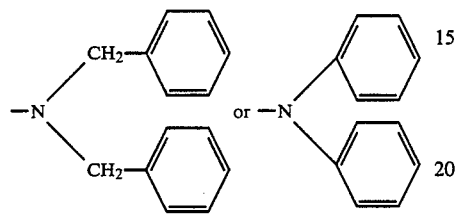

(wherein M is 0, 1, 2 or 3 and l is 1 or 2), $R_2$ is a hydrogen atom, a lower alkyl group, a lower alkoxy group or a halogen atom, $R_3$ is a hydrogen atom, a lower alkyl group or an aryl group, $R_4$ is a hydrogen atom, a lower alkyl group, a lower alkoxy group or a halogen atom, $R_5$ is an allyl group, propenyl group or

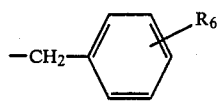

wherein said hydrazone compound is incorporated in admixture with other hydrazone compounds, oxadiazole compounds, or pyrazoline compounds (wherein $R_2$ is a lower alkyl group, a lower alkyoxy group or a halogen atom), and n is 0 or 1.

16. A photoconductive material according to claim 1 wherein $R_5$ is an allyl group or a propenyl group.

* * * * *